United States Patent [19]
Bucci et al.

[11] Patent Number: 5,290,919
[45] Date of Patent: Mar. 1, 1994

[54] HEMOGLOBIN INTRAMOLECULARLY CROSS-LINKED WITH TRIVALENT REAGENTS

[75] Inventors: Enrico Bucci; Clara Fronticelli, both of Baltimore, Md.

[73] Assignee: The University of Maryland Baltimore, Baltimore, Md.

[21] Appl. No.: 936,652

[22] Filed: Aug. 28, 1992

[51] Int. Cl.$^5$ ............................................. A61K 35/14
[52] U.S. Cl. .................................. 530/385; 530/402; 530/410
[58] Field of Search ...................... 530/385, 402, 410; 514/6

[56] References Cited

U.S. PATENT DOCUMENTS

| | | | |
|---|---|---|---|
| 4,001,401 | 1/1977 | Bonsen et al. | 530/385 |
| 4,529,719 | 7/1985 | Tye | 514/6 |
| 4,584,130 | 4/1986 | Bucci et al. | 530/385 |
| 4,600,531 | 7/1986 | Walder | 530/385 |

OTHER PUBLICATIONS

Shimizu et al., "Allosteric Effectors of Hemoglobin . . . ", Biochemistry, vol. 13, No. 4, 1974, pp. 809-814.
Bucci et al., "Hemoglobin Tetramers Stabilized with Poly Aspirins", Biomater., Artif. Cells, Immobilization Biotechnol. 20(2-4), 1992, pp. 243-252.
Cashon, R. et al., "Properties of Benzenetincarboxylic Acid . . . " Biomater. Artif. Cells, Immobilization Biotechnol. 19(2), 1991, p. 364 B1051592:109515.
Poillon, W. N. et al. "Deoxygenated Sickle Hemoglobin Modulation . . . " J. Biol. Chem., 260(26), 1985, pp. 13897-13900. Biosis 86:129432.
Banerjee et al., "Effect of Polycarboxylate Aminos on Hemoglobin", C.A. Acad. Sci., Ser. D, 277(11), 1973, pp. 963-966; CA 80(15):79315q.

Primary Examiner—Michael G. Wityshyn
Assistant Examiner—C. Sayala
Attorney, Agent, or Firm—Sughrue, Mion, Zinn, Macpeak & Seas

[57] ABSTRACT

Stroma-free hemoglobin cross-linked with reagents that mimic 2,3-diphosphoglycerate and transform stroma-free hemoglobin into a physiologically competent oxygen carrier which is retained in vivo for adequate periods of time, and thus can be used in fluids for transporting oxygen is described.

30 Claims, No Drawings

HEMOGLOBIN INTRAMOLECULARLY CROSS-LINKED WITH TRIVALENT REAGENTS

The development of the present invention was supported by the University of Maryland and NIH (HL-13164 and HL-33629).

FIELD OF THE INVENTION

The present invention relates to hemoglobin which has been intramolecularly cross-linked with reagents which transform hemoglobin into a physiologically competent oxygen carrier. As defined herein, "physiologically competent" or "physiologically acceptable" with respect to the oxygen carrier means that the oxygen carrier can absorb oxygen at the partial pressures of oxygen prevailing at the site of oxygenation of hemoglobin, e.g., in the lungs of humans or other air-breathing organisms and in the gills of fish, and release it to the tissues of the same organisms in amounts which are life supporting, at least when the organisms are in a resting state.

BACKGROUND OF THE INVENTION

1. Stroma-Free Hemoglobin

Intravenously injected (infused) crude hemolysates and extensive hemolytic processes produced in vivo by immunological reactions involving intravascular lysis of red blood cells, are known to produce a clinical syndrome characterized by disseminate intravascular coagulation. This syndrome is often fatal and is produced by the residual red blood cell walls (stroma) and their fragments, so infused into circulating blood. Stroma-free hemolysates do not show this toxicity (See Rabiner et al, *J. Exp. Med.*, 126:1127 (1967). As a result, it has been desired to use stroma-free hemoglobin as an oxygen carrier in cell-free transfusional fluids.

However, the use of stroma-free hemoglobin has the following two disadvantages. In vivo, the retention time of the stroma-free human hemoglobin is very short, i.e., it has a half-life on the order of 1-4 hours (see Rabiner et al, supra, and De Venuto et al, *Transfusion*, 17:555 (1977)). "Half-life" is defined as the time necessary to eliminate 50% of the infused hemoglobin from circulating blood. Further, outside of the red blood cells, hemoglobin has a high affinity for oxygen which, in vivo, would prevent the release, i.e., the transport, of oxygen from hemoglobin to the tissues. These disadvantages are directly the result of the molecular structure of hemoglobin. Hemoglobin is a tetrameric molecule having a molecular weight of 64,500 Daltons. The tetrameric molecule is formed of two pairs of alpha and beta subunits. The subunits are held together as a result of ionic and Van der Waals forces, and not as a result of covalent bonds. When hemoglobin is oxygenated, i.e., combined with oxygen, it readily forms alpha-beta dimers having a molecular weight of 32,250 Daltons. These dimers are not retained in vivo by the kidneys and are eliminated through the urine.

The tetrameric structure of hemoglobin also provides a binding site for 2,3-diphosphoglycerate. Inside red blood cells, 2,3-diphosphoglycerate combines with hemoglobin in order to decrease its oxygen affinity to a level compatible with oxygen transport. The binding of 2,3-diphosphoglycerate and hemoglobin is purely electrostatic and no stable covalent bonds are formed. Thus, when red blood cells are ruptured and 2,3-diphosphoglycerate is not retained inside the cells by the cell wall, it is released from hemoglobin. As a result, hemoglobin acquires a higher oxygen affinity. This prevents the transport of oxygen from hemoglobin to the tissues. The level of this higher affinity is sufficient such that the oxygen affinity can be considered "non-physiological".

Because of the many appealing qualities of hemoglobin, i.e., its ability to reversibly bind oxygen, the low viscosity of a hemoglobin solution and its easy preparation and storage for long periods of time, various attempts have been made in order to overcome the above described disadvantageous characteristics of stroma-free hemoglobin. These various attempts are discussed in more detail below.

2. Chemical Treatments for Preventing the Formation of Dimers

The formation of alpha-beta dimers, which are not retained in vivo, can be prevented by coupling the tetrameric molecules of hemoglobin with large molecular weight matrices, ranging from 20,000 to 275,000 Daltons. For example, matrices such as dextran (see Tam et al, *Can. J. Biochem.*, 56:981 (1978); and Bonneaux et al, *Experientia*, 37:884 (1981)) and hydroxyethyl starch (see Baldwin et al, *Tetrahedron*, 37:1723 (1981); and U.S. Pat. Nos. 4,412,989, 4,900,816, 4,650,786 and 4,710,488) have been employed. This coupling prevents the elimination of hemoglobin in vivo from the kidneys by way of the urine. Other types of polymeric coupling employing collagen, collagen degradation products, and gelatin as a supporting matrix have also been employed (see U.S. Pat. No. 2,591,133; U.S. Pat. No. 3,057,782; and Bowes et al, *Biochem. Biophys. Acta.*, 168:341 (1968)). However, the oxygen affinity of the resulting coupled hemoglobin is even higher than that of stroma-free hemoglobin, and thus hemoglobin coupled in this manner cannot be advantageously employed as an oxygen transport medium.

Other known treatments for preventing the formation of alpha-beta dimers are based on reactions which polymerize the tetrameric molecules of hemoglobin to form so-called "polyhemoglobins". Polyhemoglobins can be obtained using bifunctional reagents such as glutaraldehyde (see Hopwood et al, *Histochem. J.*, 2:137 (1970)) or diimidate esters (see Mock et al, *Fed. Proc.*, 34:1458 (1975); and U.S. Pat. No. 3,925,344). These bifunctional reagents form covalent bonds between the amino groups present on the surface of different hemoglobin molecules producing intermolecular cross-links. There are 40 or more of such amino groups belonging to lysyl residues on the surface of mammalian hemoglobins (44 in human hemoglobin). Thus, a large number of possible combinations of hemoglobin molecules occur. As a result, the polyhemoglobin reaction products are a heterogeneous mixture of various molecular species which differ in size and shape. The molecular weights thereof range from 64,500 to 600,000 Daltons. The separation of individual molecular species from the heterogeneous mixture is virtually impossible. In addition, although longer retention times in vivo are obtained using polyhemoglobins, the oxygen affinity thereof is higher than that of stroma-free hemoglobin.

Besides the various treatments discussed above which result in formation of heterogeneous mixtures of polyhemoglobin, reagents have been developed which are capable of producing an internal cross-link of the hemoglobin subunits with little or no formation of polyhemoglobins. More specifically, the formation of cross-links between the beta subunits of hemoglobin using 2-N-2-formyl-pyridoxal-5'-phosphate and borohydride has been carried out (see Bensch et al, *Biochem. Biophys. Res. Comm.*, 62:1123 (1975)). The oxygen affinity of the thus treated hemoglobin is decreased to levels similar to that of normal blood. However, the reagent employed therein is very difficult and costly to synthesize, and thus the method is disadvantageous.

Other reagents have been employed in order to effect internal cross-linking of the hemoglobin subunits. These reagents are commonly known as "diaspirins". Diaspirins are diesters of bis-3,5-dibromosalicylate containing succinyl, fumaryl or other dicarboxylic acid residues. These reagents produce covalent cross-links between two beta or two alpha subunits of an individual hemoglobin molecule. While better results are obtained using liganded (oxy-or carboxy-) hemoglobin, such a treatment does not characteristics of stroma-free hemoglobin, and thus can not be advantageously employed (see Walder et al, *J. Mol. Biol.*, 141:195 (1980); and U.S. Patents 4,061,736, 4,001,200;, 4,001,401, and 4,053,590). In U.S. Pat. Nos. 4,473,496 and 4,857,636, linear alpha-omega or heterocyclic polyaldehydes containing negatively charged groups are described as suitable for both decreasing the oxygen affinity of hemoglobin and for producing inter- and intramolecular cross-linking of hemoglobin. These reagents include carbohydrate-containing molecules, such as raffinose, and mono- and polyphosphorylated nucleotides partially oxidized with periodate, so as to obtain aldehydic groups. The coupling reaction is based on the formation of Shiff bases of the aldehydic groups with the amino groups of the hemoglobin molecule. The Shiff bases are then transformed into covalent bonds by reduction with sodium or potassium borohydride, or another strong reducing agent.

In U.S. Pat. No. 4,584,130, cross-linking of hemoglobin with bifunctional reagents is disclosed. The reagents disclosed therein are based on an electron withdrawing group which modulates the reactivity of two or more peripheral active groups. However, the electron withdrawing group remains within the cross-linking bridge after the reaction. In the reagent of the present application, when an electron withdrawing group is employed, it is present in the leaving group only (e.g., 3,5-dibromosalicylate), and therefore it does not remain in the cross-linking bridge after the chemical reaction of the activated carboxyls with the amino groups of the protein.

3. Chemical Treatments for Decreasing the Oxygen Affinity of Stroma-Free Hemoglobin The most widely used chemical modification of stroma-free hemoglobin so as to decrease the oxygen affinity thereof employs the use of pyridoxal-5'-phosphate and sodium or potassium borohydride (see Bensch et al, *Biochem.*, 11:3576 (1972)). The resulting product is commonly referred to as "PLP-hemoglobin" and has satisfactory oxygen affinity, i.e., oxygen affinity very near that of the red cells present in normal blood.

Other known chemical modifications of hemoglobin have been carried out using phosphoric acid derivatives of carbohydrates (e.g., glucose-6-phosphate) (see McDonald et al, *J. Biol. Chem.*, 254:702 (1979)); carbamylation (see Manning, *Meth. Enz.*, 76:159 (1981)) and carboxymethylation (see DiDonato et al, *J. Biol. Chem.*, 258:11890 (1983)). In each of these treatments, the amino-terminal end of the beta subunit of hemoglobin is permanently substituted with the above described reagents.

In addition, none of these chemical treatments discussed in this section stabilize the tetrameric structure of hemoglobin so as to prevent the formation of alpha-beta dimers. Thus, the resulting hemoglobins do not have prolonged retention times in vivo.

4. Combined Chemical Treatments for Preventing the Formation of Alpha-Beta Dimers and Decreasing the Oxygen Affinity of Stroma-Free Hemoglobin As discussed above, the production of physiologically competent stroma-free hemoglobin-based oxygen carriers necessitates two separate treatments. That is, one treatment is necessary for preventing the formation of alpha-beta dimers in vivo and a second treatment is required for decreasing its oxygen affinity. The most widely employed combination of treatments is that of reacting glutaraldehyde with PLP-hemoglobin to form pyridoxylated polyhemoglobins (see Seghal et al, *J. Surg. Res.*, 30:14 (1981). Intramolecular cross-linking of PLP-hemoglobin has also been obtained using diaspirins (see Tye et al, *Prog. Clin. Biol. Res.*, 22:41 (1983)).

It should be noted that only stroma-free hemolysates or washed red blood cells are utilized in the above-cited articles. That is, purification procedures for isolating the hemoglobin component of the stroma-free hemolysates are not described therein. Thus, what is defined as stroma-free hemoglobins therein is in actuality stroma-free hemolysates.

More specifically, about 95% of the hemolysate components is hemoglobin. The remainder consists of proteins and polypeptides whose pharmacological and immunological toxicity is not known. When used for infusion in animals, several grams of hemolysate-containing hemoglobin are injected. Thus, undesirably, hundreds of milligrams of substances of unknown biological activity are also infused into animals when employing a hemolysate.

It should also be noted that in the above-cited references, purification procedures for isolating the desired hemoglobin products from the reaction mixture are not described therein. It is impossible to avoid the presence of overreacted and underreacted hemoglobins in the reaction mixtures. These products do not have the desired functional and molecular characteristics.

For the above reasons, it is advantageous to perform chemical treatments on purified hemoglobins, and then to purify the product of the reaction.

The trivalent reagents of the present invention present clear advantage over previously employed divalent reagents of producing intramolecular cross-linked hemoglobin. Specifically, using the present trivalent cross-linking reagents, the resulting cross-linked hemoglobin of the present invention has a lower oxygen affinity, and can be obtained in a much higher yield. While the cross-link is still intramolecular, being a trivalent bridge, the hemoglobin of the present invention has been found to be more stable, not only against dissociation, but also against physical agents like heat, pH and aging. Thus, the formation of ferric hemoglobin is greatly retarded with the cross-linked hemoglobin of the present invention. This allows the use of high temperature heat treatments for eliminating pathogens, the use of lyophilization procedures and to effect storage in liquid form in the cold and at room temperature.

SUMMARY OF THE INVENTION

Accordingly, an object of the present invention is to provide a cross-linked stroma-free hemoglobin having a physiologically acceptable oxygen affinity.

Another object of the present invention is to provide a cross-linked stroma-free hemoglobin which substantially does not form alpha-beta dimers in vivo.

Still another object of the present invention is to provide a cross-linked stroma-free hemoglobin which has a half-life in vivo of at least 6 hours.

A further object of the present invention is to provide a cross-linked stroma-free hemoglobin having a low viscosity so as to facilitate fluid circulation.

A still further object of the present invention is to provide a cross-linked stroma-free hemoglobin whose is chemically stable for many months.

An additional object of the present invention is to provide a cross-linked stroma-free hemoglobin where production can be easily carried out and which can be easily stored and in a stable manner.

Another object of the present invention is to provide a cross-linked stroma-free hemoglobin which is devoid of chemical or biological toxicity.

Still another object of the present invention is to provide a reagent for cross-linking hemoglobin so as to simultaneously provide a physiologically acceptable oxygen affinity thereof and prevent the formation of alpha-beta dimers in vivo.

Also, another object of the present invention is to provide a method for cross-linking stroma-free hemoglobin using a reagent which simultaneously provides a physiologically acceptable oxygen affinity thereof and prevents the formation of alpha-beta dimers in vivo.

A still further object of the present invention is to provide a method for cross-linking a stroma-free hemoglobin which can be conducted in a single step in the absence of air and oxygen so as to obtain compounds with the desired oxygen affinity.

The above objects of the present invention have been met by the use of a cross-linking reagent of general formula (I)

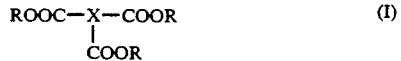
(I)

wherein R is a leaving atom or group capable of activating the carboxyl moiety to which it is attached and X is a member selected from the group consisting of a trivalent $C_{1-12}$ aliphatic group, a trivalent $C_6$ aromatic group, a trivalent $C_{5-6}$ heterocyclic group and a fused ring group.

In another embodiment of this invention, the invention provides stroma-free hemoglobin cross-linked with a cross-linking reagent of general formula (I) above.

In still another embodiment of this invention, the invention provides a method for cross-linking stroma-free hemoglobin with a cross-linking reagent of general formula (I) above.

DETAILED DESCRIPTION OF THE INVENTION

As discussed above, in an embodiment of the present invention, stroma-free hemoglobin is cross-linked with the reagent of general formula (I):

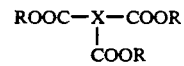
(I)

A "leaving atom or group" is well-known in the art and is an electron-rich species which can be an atom or a group of atoms which, by virtue of its capability to stabilize itself by delocalization of its excess negative charge through either resonance effects, inductive effects or charge dissipation, can easily leave, thus making room for an incoming nucleophile. In some instances, the leaving atom or group may contain an electron withdrawing group, which is lost upon the reaction with the nucleophile.

The leaving atom or group represented by R can include, among other groups, a $C_{1-12}$ alkyl group which may be substituted or unsubstituted, a substituted or unsubstituted mono or bicyclic aryl group or a substituted or unsubstituted heterocyclic group. Examples of the substituents on the alkyl, aryl or heterocyclic groups include halogen, CN, $C_{1-12}$ alkyl, phenyl which may be substituted, $NO_2$, OH or $C_{1-12}$ alkoxy, preferably $CH_3$, $C_2H_5$, $C_6H_5$ or $CH_2C_6H_5$.

Suitable examples of trivalent $C_{1-12}$ aliphatic groups for X include $C_{1-12}$ alkyl groups, $C_{2-12}$ alkenyl groups, $C_{3-12}$ alkynyl groups and $C_{3-12}$ alicyclic groups.

Suitable alkyl groups include substituted and unsubstituted straight chain and branch chain alkyl groups, such as propyl, iso-propyl, n-butyl, so-butyl, tert-butyl, pentyl, hexyl, heptyl, octyl, decyl and dodecyl.

Typical examples of alkenyl groups include substituted and unsubstituted straight chain and branch chain alkenyl groups, such as propenyl, butenyl, butadienyl, pentenyl, hexenyl, heptenyl, octenyl and dodecenyl.

Appropriate examples of alkynyl groups include substituted and unsubstituted straight and branch chain alkynyl groups, such as propynyl and butynyl groups.

Examples of substituted and unsubstituted alicyclic groups include cyclopropyl, cyclobutyl, cyclohexyl, cycloheptenyl, cyclooctyl and cyclodecyl groups. These groups may also contain unsaturated bonds as in cyclopentadienyl and cyclohexyldienyl groups.

Typical examples of aromatic groups include substituted and unsubstituted benzyl and phenyl groups.

Other appropriate examples for X include substituted and unsubstituted $C_{5-6}$ heterocyclic groups including 5- and 6-membered heterocyclic rings containing one or more of oxygen, nitrogen and sulfur atoms as heteroatoms, and examples include pyrrolyl, furanyl, thiophenyl, tetrahydrofuranyl, tetrahydrothiophenyl, pyridinyl and pyrimidinyl groups.

Examples of fused rings for X include substituted and unsubstituted fused rings, such as indole, quinoline, benzoquinoline and purine rings.

Each of the above X groups may be substituted with one or more substituents such as halogen atoms (e.g., chlorine, bromine and iodine), hydroxy groups, carboxyl groups, sulfato groups, phosphato groups, sulfonyl groups, sulfinyl groups, and the like. Longer chain substitutent groups include, for example, polyphosphates, carbohydrates, polyethylene, peptides, fatty acids and lipid moieties.

The term "hemoglobin" as used in the present invention and appended claims means hemoglobin of human, mammal, or any other animal species origin, synthetically produced hemoglobins, hemoglobins obtained by transgenic techniques and in vitro from eukaryotic or prokaryotic cell lines which have been cloned to produce hemoglobin or its subunits or its home-free submits, or hemoglobins obtained in mutant form, chemically modified form, or combined form, i.e., a combination of subunits from different species. Examples of hemoglobins include human, marine mammalian, equine, porcine, ovine, bovine, and simian hemoglobin, and additionally fish hemoglobin. Bovine hemoglobin can be obtained, for example, from blood collected from the jugular vein of a cow under sterile conditions into glass bottles containing an acid-citratedextrose (ACD) solution (i.e., containing an anticoagulant) (Fenwal Inc.) to a final 1:8 v/v. The only requirement is that the hemoglobin employed exhibit high affinity for polyanions, e.g., 2,3-diphosphoglycerate, other polyphosphates, nucleotides and polynucleotides, or other negatively charged mono- or polyvalent anions which regulate hemoglobin's oxygen affinity properties. High affinity for polyanions can be determined as described by Benesch et al, *Biochemistry*, 26:162 (1967); and Shimizu et al, *Biochemistry*, 13:809 (1974).

The hemoglobin to be treated in the present invention is stroma-free, i.e., substantially free of either cell walls or degradation products of the cell walls, or other phospholipids. Stroma-free red cell hemolysates can be used if desired, although purified hemoglobin is preferred.

The reactivity of hemoglobin with polyanions provides the means by which the reagents of the present invention can be reacted with specific sites on the hemoglobin molecule. In the present invention, trivalent reagents have been designed to bring, by virtue of their anionic characteristics, amide or enamine bond-forming groups near selected amino groups in the hemoglobin molecule so as to form intramolecular covalent cross-links of the hemoglobin subunits. Although the cross-linking is essentially intramolecular, intermolecular cross-links may also be produced and utilized.

The cross-linking bridges inserted into the hemoglobin molecule have the electronegativity characteristics necessary for simulating the presence of 2,3-diphosphoglycerate, thereby adjusting the oxygen affinity of stroma-free hemoglobin to physiologically acceptable levels.

The reagents of the present invention produce viable products by reacting both with liganded (oxy-, carboxy- or derivatives thereof) and unliganded (deoxy-) hemoglobin. In addition, ferric hemoglobin and its derivatives can also be utilized in the present invention. When the reagent of the present invention is reacted with deoxy-hemoglobin, the reaction can be performed in the presence of oxygen-absorbing chemicals, for example, sodium dithionite, without deleterious effects.

In the present invention, only a single chemical treatment is necessary for both adjusting the oxygen affinity and stabilizing the tetrameric structure of hemoglobin. Also, it is not necessary to stabilize newly introduced chemical bonds, using borohydride salts in order to form covalent bonds, as occurs with the known reactions involving aldehydes and polyaldehydes discussed above.

Since the reagents of the present invention are highly specific for selected groups on the hemoglobin molecule, reaction products within limited heterogeneity are obtained. Thus, a high yield of the desired modification product is also obtained. The specificity and necessity of only a single chemical treatment in the present invention simplifies the purification procedures as to the product obtained so that a high yield of essentially uniform molecular species is possible.

The cross-linking of hemoglobin as in the present invention prolongs the retention time of the hemoglobin after transfusion in animals (see Tye et al, *Prog. Clin. Biol. Res.*, 122:41 (1983); Greenburgh et al, *Prog. Clin. Biol. Res.*, 122:9 (1983); and Urbaitis et al, *J. Lab. Clin. Med.*, 117:115 (1991)). The presence of the cross-links also stabilizes the hemoglobins with respect to physical and chemical agents so as to allow stable and prolonged storage at low cost. Further, the cross-linked hemoglobin of the present invention is very soluble in water and all of the hemes participate in binding and transporting oxygen. Moreover, the viscosity of a 7% w/v solution of hemoglobin, i.e., a solution of hemoglobin normally used for infusion in humans or animals at 37° C., is less than that of normal blood, and thus such a solution can be advantageously employed.

The cross-linked hemoglobin of the present invention can be infused after solution in standard renal dialysis fluid (e.g., Erilyte 8306, Erika, Inc.) at a concentration of 7% w/v, after filtration through a 0.22 micron filter or some other procedure so as to ensure sterility of the fluids. In mammals, generally 10 to 100% of the circulating blood can be replaced with the cross-linked hemoglobin of the present invention.

Fluids containing the oxygen carriers of the present invention can also be used to prime the pumps necessary to drive surgical equipment, such as that which provides extracorporeal blood circulation. This will save several liters of blood presently used for this purpose. These fluids can be employed in emergency situations for shock therapy, and also have utility in veterinary uses where, in the past, sources of transfusional fluids have been scarce.

In addition, the oxygen carrier is completely soluble in water and can be used in fluids alone or with other oxygen carrier fluids and plasma expanders for transporting oxygen, for example, to isolated perfused organs, to oxygen-consuming environments, or to vial tissues in vivo as components of transfusional agents for medical and veterinary, clinical and surgical practice.

Also, the risks of transmission of infectious diseases (e.g., hepatitis, AIDS, etc.), which can occur with blood transfusions, will be absent using oxygen-carrier fluids containing the cross-linked hemoglobin of the present invention.

A. Preparation of Stroma-Free Hemoglobin

Stroma-free hemoglobin can be prepared, for example, from erythrocytes separated either from freshly drawn blood, from outdated blood, or from pelleted erythrocytes. In order to collect the erythrocytes, the blood samples are washed several times with an isotonic solution, e.g., 5.0 mM phosphate buffer, 150 mM NaCl, pH 7.5, and the plasma is separated by centrifugation at 3,000 rpm. The washed erythrocytes are then hemolyzed with an equal volume of a hypertonic solution, e.g., 5.0 mM phosphate buffer, pH 7.5. The cellular debris (stroma) still present in the hemolysate is then removed by subsequent filtration, for example, through a 0.5 micrometer Pellicon cassette and a 0.2 micrometer Pellicon cassette (Millipore) or equivalent devices. The filtered hemolysate is referred to as a "stroma-free" hemolysate since it is devoid of particles having diameters larger than 0.2 micrometer. Using a Millipore Pellicon cassette with a nominal 10,000 MW cut-off, the obtained hemolysate is concentrated and equilibrated with desired buffer, e.g., MES, acetate, MOPS, Bis-Tris, Tris or Hepes, preferably 15 mM Tris buffer, pH 8.0.

The hemoglobin is purified from non-hemoproteins, from non-hemoglobinic-hemoproteins and from organic and inorganic contaminants by absorption and subsequent elution on anionic or cationic resins. Examples of suitable anionic resins include DEAE 5PW (Waters) QUE-25/50 (Pharmacia). Examples of suitable cationic resins include 8PC 25/50 (Pharmacia) and SP 5PW (Waters). In the present invention, anionic resins are preferred since they completely remove the organic phosphates that can be bound to the hemoglobin.

Removal of organic phosphates, e.g., 2,3-diphosphoglycerate, is necessary in human hemolysates because the site of choice of the cross-linking reaction employed in the present invention is the same as that occupied by 2,3-diphosphoglycerate in hemoglobin.

The above-described procedures are generally carried out at a temperature of 4° C. to 10° C. After equilibration with the desired buffer, such as 0.05 M borate buffer, pH 9.1, the purified, stroma-free hemoglobin can be cross-linked, as described in more detail below.

B. Cross-linking of Stroma-Free Hemoglobin The term "cross-linking" as used in the present invention refers to intra-molecular cross-links which result in undissociable tetrameric hemoglobin molecules. The reagents of the present invention form stable covalent bonds with the amino groups present at the site where hemoglobin binds 2,3-diphosphoglycerate. Other sites of reaction are possible, and acceptable in producing the stabilization of the hemoglobin molecules necessary for physiological oxygen transport. When the reaction with an amino group occurs other than at the 2,3-diphosphoglycerate binding site, intermolecular cross-links can be produced. When the reaction occurs at the 2,3-diphosphoglycerate binding site, which is by far the major reaction, alpha-alpha and/or beta-beta hemoglobin subunit links are formed, which prevent the dissociation of the hemoglobin molecule into the alpha-beta dimers which, as discussed above, are rapidly eliminated in the urine after infusion. The cross-linking can be performed when hemoglobin either is liganded or unliganded. In order to cross-link the liganded form, the reagent is added to the purified stroma-free hemoglobin kept under a stream of the necessary gaseous ligands, e.g., oxygen or carbon monoxide, with continuous stirring, at between 4° C. and 10° C. In order to cross-link the unliganded form, the reagent of the present invention is added to the hemoglobin which is kept in a closed container under nitrogen or some other inert gas at atmospheric pressure. Residual oxygen is eliminated by the addition of oxygen-absorbing agents, for example, sodium dithionite in an amount of from 0.5 to 3.0 mg/ml.

The reaction of the present invention is performed using a molar equivalency or molar excess of the reagent to hemoglobin. Typically, the molar ratio of reagent to hemoglobin is 1:1 to 1:10, preferably 1:2 to 1:6. In addition, typically, the hemoglobin concentration is 3% w/v to 9% w/v, preferably 6% w/v in 0.01 M Bis-Tris buffer, pH 6.8. The reaction is allowed to proceed for an appropriate amount of time at the desired temperature, generally for about 15 minutes to 3 hours and at 10° C. to 37° C., preferably 25° C. to 30° C.

The reaction of the present invention can be terminated by passing the reaction mixture through a molecular sieving column, e.g., Sephadex column, using pressure (about 1-2 p.s.i.) generated by the same gas employed during the reaction, e.g., oxygen or carbon monoxide using a liganded hemoglobin or nitrogen using an unliganded hemoglobin. This step eliminates any excess reagent used for cross-linking and can be used for equilibrating the hemoglobin with buffer appropriate for subsequent manipulations.

For the purpose of the present invention, it is preferred to obtain pure and homogeneous products. Thus, the cross-linked hemoglobin is further purified, for example, using chromatography on anionic or cationic resins, in order to eliminate over- or under-reacted hemoglobin resulting from the chemical reaction. Examples of suitable anionic and cationic resins include DEAE 5PW (Waters), SP 5PW (Waters), or QAE-H 25/50 (Spehadex). Gradients made by mixing 5.0 mM Tris and 5.0 mM Tris and 150 mM NaCl can be used for elution. The purified cross-linked hemoglobin is collected and dialyzed three times with 1:20 v/v freshly prepared deionized water. Exposure to heat can be used to both purify the stabilized tetramers from non-reacted or over-reacted material, and to sterilize the solutions from viruses and other infective agents. This treatment is possible because the presence of the triple cross-link achieved in the present invention confers to hemoglobin a high heat stability, much higher than that of non-cross-linked material.

The incubation mixture is deoxygenated inside a fermentor, by exposure to nitrogen. Addition of 0.5 mg/ml sodium dithionite removes the last traces of oxygen. Other oxygen absorbers, such as bisulfite, metabisulfite, sulfite, can be employed for this purpose. Additives which prevent formation of aggregates can also be used. These include dithiothreitol, and reduced glutathione. This solution is kept at 60-70° C. for 7-10 hours, then rapidly cooled to 2°-5° C. Centrifugation and filtration are used to eliminate the precipitate which is formed, which contain non-cross-linked hemoglobin.

The cross-linked hemoglobin can be stored in water at −80° C. Storage at higher temperatures, between −80° and 4° C. can be carried out upon addition of dextran 70 (e.g. 6% w/v) in 0.9% w/v NaCl and/or reducing agents like ascorbic acid (e.g., 3.0 mg/ml) together with a chelating agent such as EDTA (e.g., 0.01-0.1 mg/ml) or vitamin E (e.g., 0.5 mg/ml). In this manner, the cross-linked hemoglobin is stable for weeks, at the very least, to several months.

C Analyses for Purity and Homogeneity

The purity and homogeneity of the cross-linked hemoglobin can be assessed on microzone electrophoresis using cellulose acetate membranes (Beckman Instr. Publication No. 015-083630-C). The pure compound shows a single sharp band migrating towards a positive pole at a velocity higher than that of untreated hemoglobin.

The absence of intermolecular cross-links can be assessed by gel filtration (see Ackers, *Adv. Protein Chem.*, 24:343 (1972)), ultracentrifuge analysis (see Schachman, *Biochem.*, 2:884 (1963)), or other techniques which show the absence of polyhemoglobins.

The extent of intramolecular cross-linking can be assessed using SDS urea-gel electrophoresis (see Swank et al, *Anal. Biochem.*, 39:462 (1971)). In this method, the hemoglobin is unfolded with SDS and disulfide bridges are broken so that the velocity of electrophoretic migration inside the matrix of the supporting gel is determined only by the size, i.e., the molecular weight of its monomeric subunits. In the absence of the cross-linking modifications, hemoglobin in SDS electrophoresis produces one band corresponding to a molecular weight of 16,000 Daltons, as is expected from the size of its monomeric subunits. On the other hand, if it is cross-linked, bands corresponding to polymeric units are obtained. Intramolecular cross-links produce the appearance of a 32,000 Dalton component corresponding to cross-linked subunit dimers. The non-cross-linked subunits continue to appear as a band of 16,000 Daltons. It will be easily recognized by one skilled in the art that the molecular weights given herein are as to human hemoglobin. For other species, these molecular weight values may differ somewhat but the principles involved are the same.

If the cross-linked dimer is between like subunits, the hemoglobin tetramer becomes undissociable at acid pH, e.g., at a pH of less than 7, and at neutral pH at high ionic strength, e.g., 1.0 M NaCl, because the formation of dimers under these conditions is prevented.

The presence of dimer formation in the hemoglobin solution can be ascertained by measuring the sedimentation velocity of the hemoglobin. The sedimentation constants, $S_{20,w}$, for tetramers and dimers is 4.4 and 2.8, respectively (see Schachman, supra). Alternatively, dissociation of hemoglobin into dimers can be measured by gel filtration (see Ackers, supra).

The ability of hemoglobin to reversibly bind oxygen is dependent upon the ferrous state, i.e., oxidation state, of the iron of the heme. Thus, to maximize reversible oxygen binding capability, the process of the present invention and purification steps should be conducted under conditions that do not produce irreversible oxidation of the iron atom to its ferric form. Analyses of the absorption spectra of hemoglobin in the visible region can be employed in order to estimate the amount of ferric hemoglobin present in the final product (see Benesch et al, Anal. Biochem., 11:81(1965)).

D. Determination of Oxygen Affinity

Oxygen affinity of cross-linked hemoglobin can be measured using the Hemoxyanalyser (trade name for oxygen dissociation analyzer produced by TCS-Medical Products) or the Gill cell described in Dolman et al, Anal. Biochem., 87:127 (1978).

These measurements are preferably performed at 37° C. at pH 7.4 in 0.15 M Tris buffer and 0.15 M NaCl, so as to mimic physiological conditions in vivo. Oxygen absorption by hemoglobin is characterized by two parameters. One is the value of "$P\frac{1}{2}$" i.e., the partial pressure of oxygen sufficient for saturating 50% of the hemoglobin present in solution. The other is the value of "n" in the Hill equation (see Wyman, Adv. Prot. Chem., 19:23 (1964)) which at best simulates the oxygen binding curves and which is the expression of the oxygen binding cooperativity of the hemoglobin in solution. In vivo in humans, both parameters affect the amount of oxygen transported by hemoglobin from the lungs to the tissues. Inside red blood cells, human hemoglobin has values of $P\frac{1}{2}=27$ mmHg and n near 3.0. Using the Hill equation and assuming that the partial pressure of oxygen in the lungs is 100 mmHg, and that at the tissue it is 30 mmHg (see Bard, Medical Physiology (Mosby, C.V. (1956)), these characteristics assure a delivery to the tissues of 40% of the oxygen absorbed in the lungs by hemoglobin. The same is expected from a cell-free oxygen carrier with the same characteristics. The delivery of 25% of the oxygen bound by hemoglobin is generally considered sufficient to support life in humans in a resting state. This is the transport produced by an oxygen carrier with $P\frac{1}{2}=20$ mmHg and n=1.5. For this reason, acceptable hemoglobin-based oxygen carriers are those with $P\frac{1}{2}=20$ mmHg or higher, and n=1.5 or higher. This procedure can also be used, with modifications as necessary, to determine physiological competence in species other than humans.

E. Measurement of Retention Times In Vivo of Cross-linked Hemoglobin (Intravascular Persistence)

Rabbits and rats are preferentially used for measurement of retention times in vivo of the cross-linked hemoglobin of the present invention because of their small size. After sedation and anesthetization, as necessary for maintaining the animals in a pain-free state, catheters are inserted into one carotid artery and one jugular vein. Blood is withdrawn from the artery while the liquid containing the cross-linked hemoglobin is infused through the vein, in an amount representing 40% of the blood volume. The plasma concentration of the cross-linked hemoglobin can then be measured in samples of blood withdrawn from the animal immediately after the infusion, 30 minutes later, and then hourly for 12 hours.

Preferentially, activation of the carboxyl groups in formula (I) will be through esterification with 3,5-dibromosalicylate. Other forms of activation are possible. The esters of 3,5-dibromosalicylate are known to have high specificity for the $\beta 82$ and $\alpha 99$ lysines of human hemoglobin (see Klotz et al, J. Biol. Chem., 260:16215 (1985); and Chatterjee et al, Biol. Chem., 261:9929 (1986)). The use of reagents without this specificity is inconvenient because of the large numbers of unwanted compounds which are formed during the reaction with hemoglobin. Esterification with 3,5-dibromosalicylate can be achieved as described by Razynska et al, J. Chem. Soc. Perkin Trans., 2:1531-1540 (1991).

The following examples are further provided for illustrative purposes only and are in no way intended to limit the scope of the present invention.

SYNTHESIS EXAMPLES

A. Synthesis of Tris(3,5-dibromosalicyl)-tricarballvlate (TTA)

Tricarballylic trichloride (0.01 mol) (see Emery, Ber., 22:2921 (1989)) in dry tetrahydrofuran (THF) (10 ml) was added dropwise to three equivalents of tert-butyl 3,5-dibromosalicylate (see Delaney et al, Arch. Biochem. Biophys., 28:627 (1984)) previously been treated with a stoichiometric amount of NaH in THF. The mixture was stirred for 5 hours at room temperature, and the solvent was then removed under reduced pressure. The residue was dissolved in diethyl ether and extracted several times with water. The extract was dried over $MgSO_4$, filtered and concentrated. Recrystallization from ethanol gave a pure product; m.p. 100–102° C. The resulting product (2 mmol) was dissolved in anhydrous trifluoroacetic acid (10 ml) and allowed to stand at room temperature. After 30 minutes, the solvent was removed under reduced pressure and the precipitate recrystallized from trifluoroacetic acid; m.p. 186° C. (see Razynska et al, supra).

B. Synthesis of Tris(3,5-dibromosalicyl)-benzenetricarboxylate (BTA)

Benzene tricarboxylchloride (0.01 mol) (see Emery, supra) was used as a starting material in place of TTA and the procedures described in A. above were repeated to produce tri s (3,5 -dibromosali cyl) -benzenetricarboxylate (BTA).

It should be noted that the above examples are universal for activating the free carboxyl groups of the reagents of the present invention and for conferring to the carboxyl groups the necessary specificity for the $\beta 82$ and $\alpha 99$ lysines (see Klotz et et al, *J. Biol. Chem.*, 261:9929 (1986)). et al, *J. Biol. Chem.*, 261:9929 (1986)).

Preparation of Stroma-Free Hemooloblin

One unit of outdated human blood obtained from a blood bank was poured into centrifuge containers and spun at 4° C., 3,000 rpm for 20 minutes to remove the plasma fraction. The pelleted erythrocytes were suspended and washed with 10 volumes of isotonic buffer (5.0 mM phosphate, 150 mM NaCl, pH 7.5]and centrifuged at 4° C., 3,000 rpm for 20 minutes. The supernatant was removed by aspiration. This procedure was repeated three times.

Alternatively, bovine blood was collected in an ACD solution, as above described, from the jugular vein of a cow of the Hereford breed, and the red cells were collected and washed in the same manner as described above for human blood. All of the procedures described below were applied to the resulting human and bovine blood.

The pelleted erythrocytes were then hemolyzed by addition of hypertonic buffer (5.0 mM phosphate, pH 7.5), to a final volume of 8.0 liters and filtered first through a 0.5 micrometer Millipore Pellicon cassette, then through a 0.2 micrometer Millipore Pellicon cassette, in order to separate the stroma from the stroma-free hemoglobin solution that filtered through the cassette. The stroma-free hemoglobin solution was concentrated, using a low molecular weight cut-off Millipore Pellicon cassette, with a cut-off at 10,000 MW, to a final volume producing a 10% w/v solution. The concentrated hemoglobin solution was then dialyzed using the same Pellicon cassette against 40 liters of 20 nM Tris buffer, pH 8.0.

In order to purify the hemoglobin component from the stroma-free hemolysate thus obtained, 1.0 g of the stroma-free hemoglobin was absorbed on an anionic resin (DEAE PW5, (Waters)) and chromatographed using a gradient formed by 15 mM Tris and 15 mM Tris, 500 nM NaCl, pH 8.0. A Beckman high-performance liquid chromatography (HPLC) machine was employed for the chromatography. The major peak corresponding to pure hemoglobin was collected. The various minor fractions eluted before and after the major peak were discarded. The pure stroma-free hemoglobin was dialyzed 3 times against 1:20 v/v of freshly prepared deionized-distilled water and stored at −80° C.

EXAMPLE 2

Preparation of Cross-linked Hemoglobin Using BTA and Oxy-hemoglobin

Human oxy-hemoglobin, at a concentration of 60 mg/ml in 0.05 M Tris buffer at pH 7.2 was equilibrated at 37° C., before adding 2.0 mg/ml of BTA reagent. The incubation continued with gentle stirring for 2 hours at 37° C. and was stopped with the addition of 13 mg/ml of glycyl-glycine, for 30 minutes at 37° C. During this period of time, the solution was kept under oxygen at atmospheric pressure in a closed container. The incubation mixture was dialyzed overnight against a cold 1.0 g/l glycine buffer, pH 7.6 previously equilibrated with oxygen at atmospheric pressure, then it was equilibrated with the buffers used for the chromatographic analyses as described in Example 5.

EXAMPLE 3

Preparation of Cross-linked Hemoglobin Using TTA and Oxy-hemoglobin

Human oxy-hemoglobin, at a concentration of 60 mg/ml, in 0.05 M borate buffer at pH 9.1 was equilibrated at 37° C., before adding 3.0 mg/ml of TTA reagent. The incubation continued with gentle stirring for 90 minutes at 37° C and was stopped with the addition of 13 mg/ml of glycyl-glycine, for 15 minutes at 37° C. During this period of time the solution was kept under oxygen at atmospheric pressure in a closed container. The incubation mixture was dialyzed overnight against a cold 1.0 g/l glycine buffer, pH 7.6 previously equilibrated with oxygen at atmospheric pressure, then it was equilibrated with the buffers used for the chromatographic analyses as described in Example 5.

EXAMPLE 4

Preparation of Cross-linked Hemoglobin Using TTA and Deoxy-hemoglobin

Human oxy-hemoglobin, at a concentration of 60 mg/ml, in 0.05 M borate buffer at pH 8.5 was equilibrated at 37° C. while flushing the system with nitrogen in order to remove oxygen. After flushing for 30 mintutes, 0.5 mg/ml of dithionite dissolved in 0.05 M borate buffer, pH 7.6 were added to the solution to remove the last traces of oxygen. As a result, the hemoglobin was completely deoxygenated. Then, 3.0 mg/ml of TTA reagent were added to the solution. The incubation continued with gentle stirring for 90 minutes at 37° C., and was stopped with the addition of 13 mg/ml of glycyl-glycine, for 15 minutes at 37° C. During this period of time, the solution was continuously flushed with nitrogen previously humidified by passage through a washing bottle containing deoxygenated water. The incubation mixture was dialyzed for 1 hour against cold 1.0 g/l glycine previously equilibrated with nitrogen, so as to remove the dissolved oxygen, then overnight against cold 1.0 g/l glycine buffer, pH 7.6 previously equilibrated with oxygen at atmospheric pressure. Then, the mixture was equilibrated with the buffers used for the chromatographic analyses as described in Example 5.

EXAMPLE 5

Purification of Cross-Linked Hemoglobins

As discussed above, it is preferred that the cross-linked hemoglobins of the present invention are obtained as a pure homogeneous component containing a single molecular species. Thus, a final purification step was conducted by chromatography on a DEAE PW5 column using an Altek HPLC machine. More specifically, the cross-linked hemoglobin was equilibrated with 15 mM Tris, pH 8.0, absorbed on the DEAE PW5 column and eluted using a gradient formed by 15 mM Tris and 15 mM Tris, 500 mM NaCl, pH 8.0. Three peaks were obtained, wherein the first was residual untreated hemoglobin, the second, which was the major fraction, represented cross-linked hemoglobin, and the third represented a small component of overreacted hemoglobin.

The purity of the samples was assessed by microzone electrophoresis as discussed above. The pure cross-linked hemoglobin produced single sharp bands, with different mobility than untreated hemoglobin.

In SDS-urea electrophoresis (see Swank et al, *Anal. Biochem.*, 39:462 (1971)) the purified fractions gave two bands corresponding to molecular weights of 32,000 and 16,000 Daltons, respectively. Optical scanning of the gel using a Joyce and Loeble microdensitometer indicated a relative proportion of 1:1 between the two bands, as expected from the cross-linking of only one pair of like subunits per molecule of tetrameric hemoglobin.

Sedimentation velocity experiments on the cross-linked hemoglobin gave sedimentation constants near $S_{20,w}=4.4$, both in 0.05 M phosphate buffer, pH 7.0, and in 0.05 M Bis-Tris buffer, pH 5.5. This value of the sedimentation constant is characteristic of tetrameric, non-dissociated hemoglobin. This demonstrates the inability of these cross-linked hemoglobins to dissociate into dimers normal hemoglobin in 0.05 M Bis-Tris buffer at pH 5.5 acquires a sedimentation velocity near 3.5, because it dissociates into dimers.

EXAMPLE 6

Determination of Oxygen Affinities of Various Cross-Linked Purified Hemoglobins

Cross-linked human hemoglobin purified as described in Example 5, was equilibrated with 0.15 M Tris-HCl, pH 7.4 and its oxygen affinity was measured with a Hemoscan at 37° C. Similarly, bovine hemoglobin was cross-linked and purified as described above in Examples 1–5 for human hemoglobin, and its oxygen affinity was also measured with a Hemoscan at 37° C. The results obtained are shown in the following Table:

TABLE

Oxygen Affinity of Human and Bovine Hemoglobins Treated with Either BTA or TTA

| Sample | P½ | n | % Delivery to Tissues of the Oxygen Bound by Hemoglobin in the Lungs |
|---|---|---|---|
| Human blood | 27 | 2.9 | 40 |
| Human hemoglobin (untreated) | 18 | 2.64 | 10 |
| Human hemoglobin (BTA oxy-reacted) | 21 | 2.3 | 27 |
| Bovine hemoglobin (BTA oxy-reacted) | 36 | 1.8 | 44 |
| Human hemoglobin (TTA oxy-reacted) | 16 | 1.9 | 20 |
| Human hemoglobin (TTA deoxy-reacted) | 29 | 1.5 | 35 |
| Bovine hemoglobin (TTA oxy-reacted) | 22 | 2.6 | 30 |

Note:
the last column in the Table shows values computed with the Hill equation (Wyman, Adv. Prot. Chem., 19:223 (1964)), assuming that the partial pressure of oxygen is 100 mmHg in the lungs and 30 mmHg in the tissues.

In the Table above, P½ indicates the partial pressure of oxygen necessary for saturating hemoglobin at the 50% level (i.e., P½ measures the oxygen affinity). Also, the value n is the expression of oxygen-binding cooperativity, which in normal human red cells is very close to n=3.

As shown in the Table above, most of the cross-linked stroma-free hemoglobin obtained as described above had an oxygen affinity lower than that of the corresponding untreated stroma-free hemoglobin. In addition, all of the cross-linked stroma-free human hemoglobins obtained had a value of n in the Hill plot of at least 1.5, demonstrating the persistence of a very good oxygen-binding cooperativity in the cross-linked hemoglobins.

As shown in the Table, and as above discussed, the oxygen-binding characteristics of all of the cross-linked hemoglobins assured acceptable levels of oxygen delivery to tissues.

While the invention has been described in detail and with reference to specific embodiments thereof, it will be apparent to one skilled in the art that various changes and modifications can be made therein without departing from the spirit and scope thereof.

What is claimed is:

1. Stroma-free hemoglobin intramolecularly cross-linked with a compound of the following formula (I):

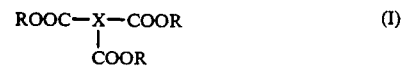

wherein R is a leaving atom or group capable of activating the carboxyl moiety to which it is attached and X is a member selected from the group consisting of a trivalent $C_{1-12}$ aliphatic group, a trivalent $C_6$ aromatic group, a trivalent $C_{5-6}$ heterocyclic group and a fused ring group.

2. The stroma-free hemoglobin as claimed in claim wherein said trivalent aliphatic group is selected from the group consisting of a $C_{1-12}$ alkyl group, a $C_{2-12}$ alkenyl group, a $C_{3-12}$ alkynyl group and a $C_{3-12}$ alicylic group.

3. The stroma-free hemoglobin as claimed in claim 2, wherein said alkyl group is selected from the group consisting of propyl, iso-propyl, n-butyl, iso-butyl, tert-butyl, pentyl, hexyl, heptyl, octyl, decyl and dodecyl.

4. The stroma-free hemoglobin as claimed in claim 2, wherein said alkenyl group is selected from the group consisting of propenyl, butenyl, butadienyl, pentenyl, hexenyl, heptenyl, octenyl and dodecenyl.

5. The stroma-free hemoglobin as claimed in claim 2, wherein said alkynyl group is selected from the group consisting of propynyl and butynyl.

6. The stroma-free hemoglobin as claimed in claim 2, wherein said alicyclic group is selected from the group consisting of cyclopropyl, cyclobutyl, cyclohexyl, cycloheptenyl, cyclooctyl and cyclodecyl.

7. The stroma-free hemoglobin as claimed in claim 1, wherein said aromatic group is selected from the group consisting of benzyl and phenyl.

8. The stroma-free hemoglobin as claimed in claim wherein said $C_{5-6}$ heterocyclic group is selected from the group consisting of pyrrolyl, furanyl, thiophenyl, tetrahydrofuranyl, tetrahydrothiophenyl, pyridinyl and pyrimidinyl.

9. The stroma-free hemoglobin as claimed in claim 1, wherein said fused ring is selected from the group consisting of an indole, quinoline, benzoquinoline and purine.

10. The stroma-free hemoglobin as claimed in claim 1, wherein R is selected from the group consisting of a hydrogen atom, a $C_{1-12}$ alkyl group which may be substituted or unsubstituted, a substituted or unsubstituted mono or bicyclic aryl group or a substituted or unsubstituted heterocyclic group.

11. The cross-linked stroma-free hemoglobin as claimed in claim 1, wherein said stroma-free hemoglobin is selected from the group consisting of human, equine, porcine, ovine, bovine, simian and fish hemoglobin.

12. The cross-linked stroma-free hemoglobin as claimed in claim wherein said stroma-free hemoglobin is bovine hemoglobin.

13. The cross-linked stroma-free hemoglobin as claimed in claim 11, wherein said stroma-free hemoglobin is human hemoglobin.

14. The cross-linked stroma-free hemoglobin as claimed in claim 1, wherein said cross-linking is carried out in the presence of oxygen.

15. The cross-linked stroma-free hemoglobin as claimed in claim 1, wherein said cross-linking is carried in the absence of oxygen.

16. A method for producing stroma-free intramolecularly cross-linked hemoglobin comprising cross-linking stroma-free hemoglobin with a compound of the following formula (I):

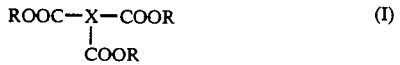

$$\text{ROOC}-\underset{\underset{\text{COOR}}{|}}{\text{X}}-\text{COOR} \qquad (I)$$

wherein R is a leaving atom or group capable of activating the carboxyl moiety to which it is attached and X is a member selected from the group consisting of a trivalent $C_{1-12}$ aliphatic group, a trivalent $C_6$ aromatic group, a trivalent $C_{5-6}$ heterocyclic group and a fused ring group.

17. The method as claimed in claim 16, wherein said trivalent aliphatic group is selected from the group consisting of a $C_{1-12}$ alkyl group, a $C_{2-12}$ alkenyl group, a $C_{3-12}$ alkynyl group and a $C_{3-12}$ alicylic group.

18. The method as claimed in claim 17, wherein said alkyl group is selected from the group consisting of propyl, iso-propyl, n-butyl, iso-butyl, tert-butyl, pentyl, hexyl, heptyl, octyl, decyl and dodecyl.

19. The method as claimed in claim 17, wherein said alkenyl group is selected from the group consisting of propenyl, butenyl, butadienyl, pentenyl, hexenyl, heptenyl, octenyl and dodecenyl.

20. The method as claimed in claim 17, wherein said alkynyl group is selected from the group consisting of propynyl and butynyl.

21. The method as claimed in claim 17, wherein said alicyclic group is selected from the group consisting of cyclopropyl, cyclobutyl, cyclohexyl, cycloheptenyl, cyclooctyl and cyclodecyl.

22. The method as claimed in claim 17, wherein said aromatic group is selected from the group consisting of benzyl and phenyl.

23. The method as claimed in claim 17, wherein said $C_{5-6}$ heterocyclic group is selected from the group consisting of pyrrolyl, furanyl, thiophenyl, tetrahydrofuranyl, tetrahydrothiophenyl, pyridinyl and pyrimidinyl.

24. The method as claimed in claim 16, wherein said fused ring is selected from the group consisting of an indole, quinoline, benzoquinoline and 25. The method as claimed in claim 16, wherein R is selected from the group consisting of a hydrogen atom, a $C_{1-12}$ alkyl group which may be substituted or unsubstituted, a substituted or unsubstituted mono or bicyclic aryl group or a substituted or unsubstituted heterocyclic group.

26. The method as claimed in claim 16, wherein said stroma-free hemoglobin is selected from the group consisting of human, equine, porcine, ovine, bovine, simian and fish hemoglobin.

27. The method as claimed in claim 26, wherein said stroma-free hemoglobin is bovine hemoglobin.

28. The method as claimed in claim 26, wherein said stroma-free hemoglobin is human hemoglobin.

29. The method as claimed in claim 16, wherein said cross-linking is carried out in the presence of oxygen.

30. The method as claimed in claim 16, wherein said cross-linking is carried in the absence of oxygen.

* * * * *